United States Patent [19]

Kilpatrick-Liverman et al.

[11] Patent Number: 5,776,475
[45] Date of Patent: Jul. 7, 1998

[54] CLEAR COSMETIC STICK COMPOSITION CONTAINING SUCROSE ESTERS AND METHOD OF USE

[75] Inventors: LaTonya Kilpatrick-Liverman, Princeton; Lynne Ann Miller, Sayreville, both of N.J.

[73] Assignee: Colgate-Palmolive Company, New York, N.Y.

[21] Appl. No.: 800,914

[22] Filed: Feb. 13, 1997

Related U.S. Application Data

[60] Provisional application No. 60/012,189 Feb. 23, 1996.

[51] Int. Cl.$^6$ .............................................. A61K 7/32
[52] U.S. Cl. .................................... 424/401; 424/65
[58] Field of Search .................................. 424/401, 65

[56] References Cited

U.S. PATENT DOCUMENTS

| | | | |
|---|---|---|---|
| 4,268,498 | 5/1981 | Gedeon et al. | 424/59 |
| 4,322,400 | 3/1982 | Yuhas | 424/59 |
| 4,759,924 | 7/1988 | Luebbe et al. | 424/42 |
| 4,944,937 | 7/1990 | McCall | 424/65 |
| 5,114,717 | 5/1992 | Kuznitz et al. | 424/401 |
| 5,120,541 | 6/1992 | Macaulay et al. | 424/401 |
| 5,128,123 | 7/1992 | Brewster et al. | 424/65 |
| 5,368,848 | 11/1994 | Brazinsky et al. | 424/65 |
| 5,424,070 | 6/1995 | Kasat et al. | 424/401 |
| 5,458,880 | 10/1995 | Kasat et al. | 424/401 |
| 5,462,736 | 10/1995 | Rech et al. | 424/401 |

FOREIGN PATENT DOCUMENTS

| | | |
|---|---|---|
| 96/37185 | 11/1996 | WIPO . |
| 96/37186 | 11/1996 | WIPO . |

*Primary Examiner*—Thurman K. Page
*Assistant Examiner*—D. Faulkner
*Attorney, Agent, or Firm*—Richard J. Ancel; Rosemary M. Miano

[57] ABSTRACT

Disclosed are clear, soap-gelled cosmetic (for example, deodorant) stick compositions, containing alcohol and water, and also including at least one sucrose ester (for example, sucrose cocoate) as a clarifying agent. The compositions can also include various cosmetically active ingredients, including deodorant active materials (fragrance, Triclosan, etc.). The compositions have superior clarity as originally formed and over extended periods of time after being manufactured, and have superior pay-out properties.

30 Claims, No Drawings

CLEAR COSMETIC STICK COMPOSITION CONTAINING SUCROSE ESTERS AND METHOD OF USE

This application is a provisional of 60/012.189, filed Feb 23, 1996.

BACKGROUND OF THE INVENTION

The present invention relates to a clear cosmetic stick composition base, in which a cosmetically active ingredient can be incorporated to form a clear cosmetic stick composition, as well as such clear cosmetic stick composition (for example, a deodorant solid stick composition) having the cosmetically active ingredient incorporated therein.

More specifically, the present invention relates to cosmetic solid stick compositions containing an alcohol (for example, a monohydric alcohol, such as ethanol, or polyhydric alcohol, such as propylene glycol) and water, and gelled with a soap gelling agent (for example, an alkali metal salt of a saturated fatty acid). In particular, the present invention relates to clear cosmetic solid stick compositions with improved clarity, so as to achieve an improved appearance, which retain such improved clarity over an extended period of time, and which have improved pay-out (that is, improved deposition of the solid stick product on a surface (for example, the skin) upon which the composition is rubbed).

The present invention is especially related to clear, soap-gelled deodorant stick compositions that are clear and maintain such clarity for extended periods of time, and which have improved pay-out, the compositions containing a deodorant active material such as a fragrance and/or an antibacterial agent. However, the present invention is not limited to clear, soap-gelled deodorant stick compositions, but has general applicability to other clear sticks. That is, depending on the cosmetically active ingredient incorporated in the stick composition (for example, a deodorant active ingredient, an insect repellent, a sunscreen, an emollient, etc.), the cosmetic stick composition according to the present invention can be a deodorant stick composition, an insect repellent stick, a sunscreen stick, a skin care stick, etc.

It has been desired to provide soap-gelled, clear cosmetic stick compositions, such as soap-gelled, clear deodorant solid stick compositions, which retain clarity over an extended period of time so as to have a long shelf life. Such clear stick compositions have widespread consumer appeal. It has been desired to provide such clear stick compositions which maintain clarity for extended periods of time, for example, from prior to being purchased by the consumer (for example, from the time of manufacture) and until the product has been used up by the consumer. In particular, it has been desired to provide such a clear stick composition, having a long shelf life, which avoids crystals forming in the stick over, for example, the shelf life of the composition.

U.S. Pat. No. 4,268,498 to Gedeon, et al., the contents of which are incorporated herein by reference in their entirety, discloses a substantially clear cosmetic stick containing specific amounts of a polyoxyethylene (17-23)-glucose-fatty acid ester; a polyoxyethylene (20-26) ether of a long chain alcohol; a polyoxypropylene (2-5) ether of a long chain alcohol; a sodium salt of a fatty acid; propylene glycol; lower alkyl ester of fatty acids; water and cosmetically active ingredient. This patent document discloses that the composition can accommodate high levels of cosmetically acceptable ingredients such as fragrances and sunscreen.

U.S. Pat. No. 5,462,736 to Rech, et al., the contents of which are incorporated herein by reference in their entirety, discloses a clear, crystal-free, soap-gelled cosmetic stick composition containing a soap gelling agent; at least two aliphatic polyhydric alcohols that are solvents for the soap gelling agent and that have a relatively large and relatively small molecular weight, respectively; a propoxylated ether that is a further solvent for the soap gelling agent, such as a propoxylated butyl ether; water; and a clarifying agent, the clarifying agent being a mixture of (a) a propoxylated fatty alcohol, such as a propoxylated myristyl ether, and (b) a water soluble, N-substituted aliphatic fatty acid amide surfactant (for example, a combination of cocamide DEA and cocoyl sarcosine). This patent discloses that this stick composition has improved surface aesthetics and improved pay-out, and has less pullaway from the container.

Other patents disclosing clear cosmetic stick compositions include the following, the contents of each of which are incorporated herein by reference in their entirety: U.S. Pat. No. 4,759,924 to Luebbe, et al.; U.S. Pat. No. 5,114,717 to Kuznitz, et al.; U.S. Pat. No. 5,120,541 to Macaulay, et al.; U.S. Pat. No. 5,128,123 to Brewster, et al.; U.S. Pat. No. 5,424,070 to Kasat, et al., U.S. Pat. No. 5,458,880 to Kasat, et al., and U.S. Pat. No. 5,368,848 to Brazinsky, et al.

U.S. patent application No. 08/448,101, filed May 23, 1995, to Kilpatrick-Liverman, et al., discloses, inter alia, incorporating ethoxylated surfactants, dimethicone copolyols or polymers of polyethylene glycols in soap-gelled cosmetic stick formulations containing propylene glycol and water, in order to provide products with improved clarity and pliability. U.S. patent application Serial No. 07/448,104, filed May 23, 1995, to Shevade, et al., discloses, inter alia, clear cosmetic compositions containing a combination of anionic and non-ionic surfactants as a clarifying agent of a soap-gelled cosmetic stick composition containing propylene glycol and water.

Notwithstanding the foregoing, it is still desired to provide a clear cosmetic stick composition, such as a clear deodorant stick composition, which is clear and maintains clarity over extended periods of time, and which has improved pay-out (increased depositing of the composition when rubbed on the skin).

Accordingly, it is an object of the present invention to provide a cosmetic stick composition base, in which a cosmetically active ingredient can be incorporated to provide a cosmetic stick composition, the base including water and alcohol and being gelled utilizing a soap gelling agent, the base being clear, with improved clarity, and which maintains such clarity over extended periods of time, in particular, over the shelf life and period of use by a consumer, and a method of use thereof.

It is a further object of the present invention to provide a clear cosmetic stick composition, which is clear even when a cosmetically active material is incorporated therein, and which maintains clarity for relatively long periods of time (so as to have a relatively long shelf life as a clear product), and a method of use of such composition.

It is a further object of the present invention to provide a clear cosmetic stick composition, such as a clear deodorant stick composition, containing alcohol and water, and gelled by a soap (such as alkali metal salts of fatty acids), which maintains clarity for long periods of time, and wherein crystals do not form within the composition over these long periods of time, and a method of using such composition.

It is a further object of the present invention to provide a cosmetic solid stick composition that is clear when having

3 cosmetically active materials incorporated therein and that maintains such clarity, and that has improved pay-out (so as to deposit on, for example, the skin, a satisfactory amount of the cosmetically active material).

It is a further object of the present invention to provide a clear deodorant stick composition having deodorant active material incorporated therein, which can be applied, for example, to axillary regions of the body to reduce or avoid axillary malodor, the composition depositing a satisfactory amount of deodorant active material, the composition maintaining clarity for extended periods of time, and a method of use of such composition.

SUMMARY OF THE INVENTION

The foregoing objects are achieved, according to the present invention, by forming a cosmetic stick composition comprising water and at least one alcohol, and gelled with at least one soap gelling agent, wherein the composition also contains at least one sucrose ester as a clarifying agent in an amount sufficient to provide a clear stick composition. Illustratively, and not by way of limitation, the at least one sucrose ester should be included in the composition in an amount between 0.2%–2.0% by weight, of the total weight of the cosmetic stick composition. Preferably, the range of the amount of the at least one sucrose ester incorporated in the composition is 0.5%–1.0% by weight, of the total weight of the composition.

The clear stick composition according to the present invention can include various active materials, including sunscreens, deodorant active materials, insect repellents, emollients, etc. As can be appreciated, depending on the active material incorporated, the product formed would be a sun protection stick, deodorant stick, insect repellent stick, etc. As for various active materials which can be incorporated in the stick composition according to the present invention, and amounts of these materials, see U.S. Pat. No. 4,322,400 to Yuhas, the contents of which are incorporated herein by reference in their entirety, and U.S. Pat. No. 5,128,123 to Brewster, et al., contents of which have previously been incorporated herein by reference in their entirety.

DETAILED DESCRIPTION OF THE INVENTION

In terms of the present disclosure, a cosmetic stick composition comprising water and at least one alcohol, and gelled with at least one soap gelling agent, wherein the composition also contains at least one sucrose ester as a clarifying agent, in an amount sufficient to provide a clear stick composition is formed.

A base composition is selected which contains water and at least one alcohol which is gelled with salts (soaps) of fatty acids including saturated or unsaturated fatty acids.

The alcohol included in the solid stick composition of the present invention can be a monohydric and/or polyhydric alcohol (for example, ethanol as a monohydric alcohol, and propylene glycol and/or dipropylene glycol as polyhydric alcohols). Various polyhydric alcohols which can be used in soap-gelled alcohol-and water-containing stick compositions are described in U.S. Pat. No. 4,759,924, the contents of which have previously been incorporated herein by reference in their entirety, and can also be used in the present invention. These include especially propylene glycol.

A necessary component of the cosmetic stick composition according to the present invention is a soap gel-forming agent. Sodium salts of fatty acids of carbon chain length $C_{12}$–$C_{22}$, for example, sodium salts of saturated fatty acids having the above-mentioned carbon chain lengths, can be utilized as the gel-forming agent. Preferred gel-forming agents according to the present invention include sodium salts (that is, soaps) of relatively long-length-carbon-chain saturated fatty acids (for example, sodium salts of saturated fatty acids having carbon chain lengths of $C_{20}$ and/or $C_{22}$). The fatty acid portions of the soap can include a mixture of different saturated fatty acids of carbon chain length in the range $C_{12}$–$C_{22}$, preferably including some $C_{20}$ and/or $C_{22}$ in an amount of from 15–25 percent of the total fatty acid content. By utilizing such relatively long-chain-length fatty acids ($C_{20}$ and/or $C_{22}$), a product is provided having a relatively high melting temperature, and, correspondingly, relatively greater stability.

Preferred gel-forming agents according to the present invention include mixtures of sodium fatty acid soaps, having different fatty acid portions. For example, the soap gel-forming agent can be a mixture of sodium laurate, sodium myristate, sodium palmitate, sodium stearate, sodium arachidate and sodium behenate, with the sodium fatty acid soaps respectively preferably having the following distribution shown in Table 1:

TABLE 1

| Fatty Acid Soap | % (By Weight, of the Soap Mixture) |
|---|---|
| Sodium laurate | 2% |
| Sodium myristate | 4–7% |
| Sodium palmitate | 35–44% |
| Sodium stearate | 31–44% |
| Sodium arachidate | 7–9% |
| Sodium behenate | 8–10% |

This mixture of sodium fatty acid soaps, having the desired distribution, can be provided in any number of ways known in the art. For example, pure sodium laurate, pure sodium myristate, etc., can be mixed together in desired proportions. Or different mixtures of sodium fatty acid soaps (for example, commercial grade sodium stearate, containing sodium stearate, sodium palmitate, etc., and another mixture of sodium fatty acid soaps) can be combined to provide the desired distribution.

The foregoing fatty acid soap distribution of the soap gel-forming agent is illustrative, and not limiting the present invention.

Illustratively, and not limit by way of limitation, the cosmetic stick composition base according to the present invention, in which the cosmetically active ingredient can be incorporated, can include the following amounts (in percent by weight, of the total weight of the composition) of other components than the at least one sucrose ester:

alcohol (for example, propylene glycol): 55–80%
water: 9–25%
soap: 4–10%

Preferably, the soap gelling agent of the composition of the present invention contains salts of saturated or unsaturated fatty acids having carbon chain lengths of $C_{12}$–$C_{22}$, with at least some of these salts being salts of fatty acids having carbon chain length of $C_{20}$ and/or $C_{22}$. Utilizing, for example, sodium salts of long-chain saturated fatty acids of carbon chain lengths of $C_{20}$ and/or $C_{22}$ provides a product having a higher gelling temperature and improved stability.

The sucrose ester which is added in an amount between 0.2 percent–2.0 percent by weight of the total weight of the cosmetic composition has a sucrose portion and an acid portion. The acid portion of the ester is, illustratively, derived from a fatty acid (saturated or unsaturated) that has a carbon chain length from $C_8$ to $C_{22}$. Preferably, the acid portion of the sucrose ester (for example, derived from a fatty acid) has a carbon chain length from $C_{12}$ to $C_{18}$, more preferably from $C_{12}$ to $C_{14}$, to improve the clarity of the stick composition. As a specific illustration, the at least one sucrose ester can be sucrose cocoate. Sucrose cocoate is an illustrative sucrose ester which can be utilized in the present invention, but the present invention is not limited thereto.

It is desirable not to include in the stick composition of the present invention components (materials) which would disadvantageously affect clarity of the final product. Accordingly, it is preferred that materials which reduce clarity are not incorporated in the composition of the present invention.

With the foregoing caveat, compositions according to the present invention can include various additional materials conventionally included in cosmetic stick compositions. Various materials incorporated in stick compositions are disclosed in U.S. Pat. No. 4,759,924 and U.S. Pat. No. 5,128,123, the contents of each of which have previously been incorporated herein by reference in their entirety. The additional materials can include, illustratively (and not by way of limitation), polyols, fatty alcohols, alkanolamide, color (dyes), essential oils, soluble inorganic salts of sodium and potassium, etc.

Accordingly, by the present invention, which incorporates at least one sucrose ester in the soap-gelled stick composition containing water and alcohol, a solid stick composition is achieved that is clear, with improved clarity, and maintains clarity over relatively long periods of time; and that has improved pay-out. Moreover, various cosmetically active ingredients, such as deodorant active materials, can be incorporated in the composition, so as to provide, for example, clear deodorant stick compositions that retain clarity over long periods of time, while having improved pay-out.

The present invention is directed, most generally, to clear cosmetic stick composition bases, in which a cosmetically active ingredient can be included to provide a clear cosmetic stick composition. By clear, we mean the usual dictionary definition of this term. Thus, a clear stick, like glass, allows for ready viewing of objects behind it. By contrast, a translucent cosmetic stick, although allowing light to pass through, causes the light to be so scattered that it will be impossible to clearly identify objects behind the translucent stick. Opaque sticks do not permit the light to pass therethrough. Thus, according to the present invention there is a distinction between, for example, "clear" and "translucent" cosmetic sticks.

Generally, a one cm slice of the stick composition according to the present invention will permit over a 60% transmittance of light of any wavelength in the range of 600–900 nm. However, we do not want to be limited to such 60% transmittance, relying on the usual dictionary definition of "clear" as discussed previously and known in the present art.

The present invention contemplates clear cosmetic stick compositions (for example, clear deodorant solid stick compositions) and the base therefor, containing alcohol and water, and gelled with salts (soaps) of fatty acids (saturated or unsaturated fatty acids), the compositions (and base) further including at least one sucrose ester for clarifying the composition. The sucrose ester has been previously discussed, an illustrative sucrose ester being sucrose cocoate. However, the composition of the present invention is not limited to the use of such sucrose cocoate.

Other materials can be included in the clear stick compositions according to the present invention, and include various cosmetically active materials. For example, and not limiting, stick compositions according to the present invention can include cosmetically active materials such as deodorant active materials (including fragrances and antibacterial agents), sunscreens, skin conditioners, nail conditioners and the like. For purposes of the present invention, these other materials should not unsatisfactorily affect clarity, and, where appropriate, should be able to be safely applied to the human body.

As indicated previously, compositions according to the present invention have use as underarm deodorant compositions (for example, by application to axillary regions of the human body), when having deodorant active materials incorporated therein. Various deodorant active materials which can be included in the compositions according to the present invention, and the amounts of these materials, are described in U.S. Pat. No. 4,759,924, the contents of which have previously been incorporated herein by reference in their entirety, and include (but are not limited to) fragrances (for example, perfumes) and antibacterial agents (for example, bacteriostats and bactericides), among others. For example, a deodorant active material useful as an antibacterial agent in the present invention is 2-4-4'-trichloro-2'-hydroxydiphenyl ether (CTFA name: Triclosan). An antibacterial agent such as Triclosan is not a required component of the composition, even where the composition is a deodorant stick composition to be applied to the axillary regions to combat body malodor.

Other ingredients such as dyes, pigments, coloring agents, etc., which do not disadvantageously affect the clarity of the solid stick compositions of the present invention, can desirably be incorporated in the soap-gelled compositions of the present invention, in amounts as conventionally incorporated and as discussed in U.S. Pat. No. 4,759,924.

The compositions according to the present invention are manufactured by processing techniques conventional in the art. Specifically, the solid components of the composition are melted and these melted components are mixed. Preferably, the fragrance (if any) is added close to the end of the manufacturing process (for example, is the last component added), with the previously mixed components being cooled to a lower temperature (while still maintaining a melt) prior to adding the fragrance, so as to limit any volatilization of the fragrance. While still in the liquid state, the composition is filled in a dispensing package (as conventional in the art) and then cooled to solidify the product in the package.

The compositions according to the present invention are utilized by conventional techniques. For example, when utilizing compositions according to the present invention as an axillary deodorant solid stick, having deodorant active materials (such as Triclosan and/or a fragrance) incorporated therein, the solid stick product is elevated out of the dispensing package so as to expose the end of the stick product, and the exposed portion of the stick product is then rubbed against, for example, the axillary region of the human body so as to deposit the deodorant active materials on the skin in the axillary region. By use of the at least one sucrose ester as the clarifying agent, a composition having good pay-out is achieved. That is, in various prior compositions, only small amounts of the composition (and, correspondingly, only small amounts of the deodorant active materials) are deposited on the skin when the composition is rubbed against the axillary region of the human body. The composition of the present invention, containing the at least one sucrose ester, deposits increased amounts of the composition when rubbed against, for example, the axillary region of the human body, so as to deposit increased amounts of the active materials.

While, in the foregoing, the present invention has been described in terms of a deodorant solid stick composition for use in axillary regions, the present invention is not so limited; and the cosmetic stick composition according to the present invention has various uses depending on the active material incorporated therein, including (but not limited to) as a deodorant for other parts of the body, sun protection stick, insect repellant, skin softener, etc.

While the present invention is described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Thus, while the description is most specific with respect to clear deodorant stick compositions, the present invention is not limited to deodorant compositions, but includes within its scope various cosmetic products, depending on the cosmetically active material incorporated in the stick composition.

Throughout the present disclosure, where the invention is described as including or comprising components or materials, or as including or comprising processing steps, it is contemplated by the inventors that the present invention also consists essentially of, or consists of, the recited components or materials, or recited processing steps. Accordingly, throughout the present disclosure any described composition of the present invention can consist essentially of, or consist of, the recited components or materials, and any described processing technique can consist essentially of, or consist of, the recited processing steps.

Throughout the present disclosure, various of the components of the disclosed compositions are denoted by their name in the CTFA International Cosmetic Ingredient Dictionary (4th Ed. 1991), the contents of which are incorporated herein by reference in their entirety.

In the following, specific examples of compositions within the scope of the present invention will be set forth. Of course, these specific examples are illustrative of the present invention and are not limiting. In the following examples, the stated percentages are percentages by weight of the stated component, relative to the total weight of the composition. The names utilized are the CTFA names for the ingredients, where applicable.

In the following Examples I and II, the sucrose ester respectively is Grilloten 87K and Grilloten 65K, each a sucrose cocoate surfactant manufactured by Rita Corp., Woodstock, Ill.

EXAMPLE I

| Ingredients | % by weight, of the total weight of the composition |
| --- | --- |
| Sodium Stearate | 6 |
| Propylene Glycol | 79.5 |
| Water | 13.5–14.0 |
| Sucrose Ester | 0.5–1.0 |

EXAMPLE II

| Ingredients | % by weight, of the total weight of the composition |
| --- | --- |
| Sodium Stearate | 6 |
| Propylene Glycol | 79.5 |
| Water | 13.5–14.0 |
| Sucrose Ester | 0.5–1.0 |

Pay-out measurements can be carried out using a rub tester instrument. A constant weight is applied to a sample of the stick composition, and the sample is then stroked across a smooth or roughened surface at a constant rate for a given number of strokes. The amount of composition deposited is calculated by measuring the difference in the substrate weight before and after rubbing. This procedure should be repeated for at least 5 trials or until the amount of composition deposited differed by less than 3 mg.

Accordingly, by incorporating the sucrose ester as part of the cosmetic stick composition base containing alcohol and water, and gelled with a soap-gelling agent, a clear cosmetic stick composition containing cosmetically active material and such base, which maintains improved clarity over extended periods of time, while having good pay-out, is achieved. Various cosmetically active materials, including deodorant active materials, such as conventional deodorant active materials, can be incorporated in the stick composition, so as to provide, for example, a deodorant stick, maintaining good clarity and pay-out.

While we have shown and described several embodiments in accordance with the present invention, it is understood that the same is not limited thereto, but is susceptible of numerous changes and modifications as known to those skilled in the art. Therefore, we do not wish to be limited to the details shown and described herein, but intend to cover all such changes and modifications as are encompassed by the scope of the appended claims.

We claim:

1. A base, for a clear cosmetic composition, comprising water in the amount of 9–25% and at least one alcohol, and gelled with at least one soap gelling agent, the composition also containing at least one sucrose ester in the amount of 0.2–2% as a clarifying agent, in an amount sufficient to provide a clear stick composition.

2. The clear cosmetic stick composition base according to claim 1, wherein the acid portion of the at least one sucrose ester has a carbon chain length from $C_8$ to $C_{22}$.

3. The clear cosmetic stick composition base according to claim 2, wherein the acid portion of the at least one sucrose ester has a carbon chain length from $C_{12}$ to $C_{14}$.

4. The clear cosmetic stick composition base according to claim 3, wherein the at least one sucrose ester is sucrose cocoate.

5. The clear cosmetic stick composition base according to claim 4, wherein the sucrose cocoate is included in the composition base in an amount of 0.2–2.0% by weight, of the total weight of the cosmetic stick composition.

6. The clear cosmetic stick composition base according to claim 4, wherein the sucrose cocoate is included in the composition base in an amount of 0.5–1.0% by weight, of the total weight of the cosmetic stick composition.

7. A clear cosmetic stick composition comprising the cosmetic stick composition base according to claim 6 further comprising at least one cosmetically active ingredient, the at least one cosmetically active ingredient being included in the stick composition in an amount sufficient to have a cosmetic effect.

8. The clear cosmetic stick composition according to claim 7, wherein the at least one cosmetically active ingredient is at least one deodorant active material, whereby the stick composition is a clear deodorant stick composition.

9. The clear deodorant stick composition according to claim 8, wherein the at least one soap gelling agent is at least one alkali metal salt of a fatty acid.

10. The clear deodorant stick composition according to claim 9, wherein the at least one alcohol includes propylene glycol.

11. The clear deodorant stick composition according to claim 10, wherein the fatty acid component of the at least one alkali metal salt of a fatty acid has a carbon chain length in a range of $C_{12}$–$C_{22}$, with from 15–25 percent of the fatty acid component being at least one of $C_{20}$ fatty acid and $C_{22}$ fatty acid.

12. The clear cosmetic stick composition base according to claim 3, wherein the at least one sucrose ester is included in the composition base in an amount of 0.2–2.0% by weight, of the total weight of the cosmetic stick composition.

13. The clear cosmetic stick composition base according to claim 1, wherein the at least one sucrose ester is included in the composition base in an amount of 0.2–2.0% by weight of the total weight of the cosmetic stick composition.

14. A clear cosmetic stick composition comprising the cosmetic stick composition base according to claim 13, and at least one cosmetically active ingredient, the at least one cosmetically active ingredient being included in the stick composition in an amount sufficient to have a cosmetic effect.

15. The clear cosmetic stick composition according to claim 14, wherein the at least one cosmetically active ingredient is at least one deodorant active material, whereby the stick composition is a clear deodorant stick composition.

16. A clear cosmetic stick composition, comprising:

(a) at least one cosmetically active material, in an amount sufficient to have a cosmetically active effect;

(b) at least one alcohol, in an amount of 55–80% by weight, of the total weight of the composition;

(c) a soap gelling agent, in an amount of 10% by weight, of the total weight of the composition;

(d) water, in an amount of 9–25% by weight, of the total weight of the composition; and (e) at least one sucrose ester, in an amount of 0.2–2.0% by weight, of the total weight of the composition.

17. The clear cosmetic stick composition according to claim 16, wherein the at least one sucrose ester is sucrose cocoate.

18. The clear cosmetic stick composition according to claim 16, wherein the acid portion of the at least one sucrose ester has a carbon chain length from $C_{12}$ to $C_{14}$.

19. A clear deodorant stick composition, comprising:

(a) at least one deodorant active material, in an amount sufficient to have a deodorant active effect;

(b) at least one alcohol, in an amount of 55–80% by weight, of the total weight of the composition;

(c) a soap gelling agent, in an amount of 4–10% by weight, of the total weight of the composition;

(d) water, in an amount of 9–25% by weight, of the total weight of the composition; and (e) at least one sucrose ester, in an amount of 0.2–2.0% by weight, of the total weight of the composition.

20. The clear deodorant stick composition according to claim 19, wherein the at least one sucrose ester is sucrose cocoate.

21. The clear deodorant stick composition according to claim 19, wherein the acid portion of the at least one sucrose ester has a carbon chain length from $C_{12}$ to $C_{14}$.

22. A method of reducing human body malodor, comprising applying the clear deodorant stick composition of claim 21 to axillary regions of the human body.

23. A method of reducing human body malodor, comprising applying the clear deodorant stick composition of claim 20 to axillary regions of the human body.

24. A method of reducing human body malodor, comprising applying the clear deodorant stick composition of claim 19 to axillary regions of the human body.

25. A method of reducing human body malodor, comprising applying the clear deodorant stick composition of claim 11 to axillary regions of the human body.

26. A method of reducing human body malodor, comprising applying the clear deodorant stick composition of claim 10 to axillary regions of the human body.

27. A clear cosmetic stick composition base made by combining water, at least one alcohol, at least one soap gelling agent and at least one sucrose ester.

28. A clear cosmetic composition according to claim 27 wherein the acid portion of the sucrose ester has a carbon chain length of $C_8$–$C_{22}$.

29. A clear cosmetic composition according to claim 27 wherein the composition is made with the inclusion of at least one cosmetically active material.

30. A clear cosmetic composition according to claim 27 wherein the cosmetically active material is a deodorant active material.

* * * * *